United States Patent
Nanri et al.

(10) Patent No.: US 9,603,845 B2
(45) Date of Patent: Mar. 28, 2017

(54) PROPHYLACTIC AGENT AND/OR THERAPEUTIC AGENT FOR STRESS URINARY INCONTINENCE

(71) Applicant: TAIHO PHARMACEUTICAL CO., LTD., Tokyo (JP)

(72) Inventors: Masato Nanri, Tokushima (JP); Fukumitsu Sakakibara, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/388,289

(22) PCT Filed: May 14, 2013

(86) PCT No.: PCT/JP2013/063409
§ 371 (c)(1),
(2) Date: Sep. 26, 2014

(87) PCT Pub. No.: WO2013/172339
PCT Pub. Date: Nov. 21, 2013

(65) Prior Publication Data
US 2015/0051250 A1   Feb. 19, 2015

(30) Foreign Application Priority Data
May 15, 2012   (JP) ................................. 2012-111843

(51) Int. Cl.
*A61K 31/4465*   (2006.01)
*C07D 211/50*   (2006.01)

(52) U.S. Cl.
CPC ........ *A61K 31/4465* (2013.01); *C07D 211/50* (2013.01)

(58) Field of Classification Search
None
See application file for complete search history.

(56) References Cited

FOREIGN PATENT DOCUMENTS

| | | |
|---|---|---|
| GB | 2 031 727 A | 4/1980 |
| JP | 55-55117 | 4/1980 |
| JP | 62-039567 | 2/1987 |

OTHER PUBLICATIONS

Wuest et al., 145(5) British J. of Pharma. 608-619 (2005).*
Okada et al., 44(1) Hinyokika Kiyo (Acta. Urol. Jap.) 65-9 (Jan. 1998) (Abstract).*
Okada et al., "Clinical Effect of Propiverine in Patients with Urge or Stress Incontinence", Acta Urol. Jpn., 1998, vol. 44, No. 1, pp. 65-69.
DeLancey, "The pathophysiology of stress urinary incontinence in women and its implications for surgical treatment", World J Urol, 1997, vol. 15, pp. 268-274.
Marunaka et al., "Gas Chromatographic-Mass Fragmentographic Determination of Propiverine and its Metabolites in Plasma and Urine", Journal of Chromatography, 1987, vol. 420, pp. 43-52.
Haustein et al., "On the Pharmacokinetics and Metabolism of Propiverine in Man", European Journal of Drug Metabolism and Pharmacokinetics, 1998, vol. 13, No. 2, pp. 81-90.
Search Report cited in PCT/JP2013/063409 dated Aug. 13, 2013, 2 pages.
K.E. Andersson et al., The pharmacological treatment of urinary incontinence, BJU International, 1999, 84, 923-947.
Extended European Search Report dated Sep. 24, 2015 for the corresponding EP Application No. 13790782.0, 5 pages.
Melinda Wuest et al., "Propiverine and Metabolites: Differences in Binding to Muscarinic Receptors and in Functional Models of Detrusor Contraction", Naunyn-Schmiedeberg's Arch Pharmacol, vol. 374, No. 2, Oct. 20, 2006, pp. 87-97.
Mizumachi et al., Journal of the Japanese Continence Society, vol. 20-1, p. 176, 2009, English translation attached.

* cited by examiner

*Primary Examiner* — Timothy R Rozof
(74) *Attorney, Agent, or Firm* — Rothwell, Figg, Ernst & Manbeck, P.C.

(57) ABSTRACT

An object to be solved by the present invention is to provide a superior prophylactic agent and/or therapeutic agent for stress urinary incontinence. The present invention provides a prophylactic agent and/or a therapeutic agent for stress urinary incontinence comprising an effective amount of 4-piperidyl diphenylpropoxyacetate or a salt thereof, and a pharmaceutical carrier.

1 Claim, 1 Drawing Sheet

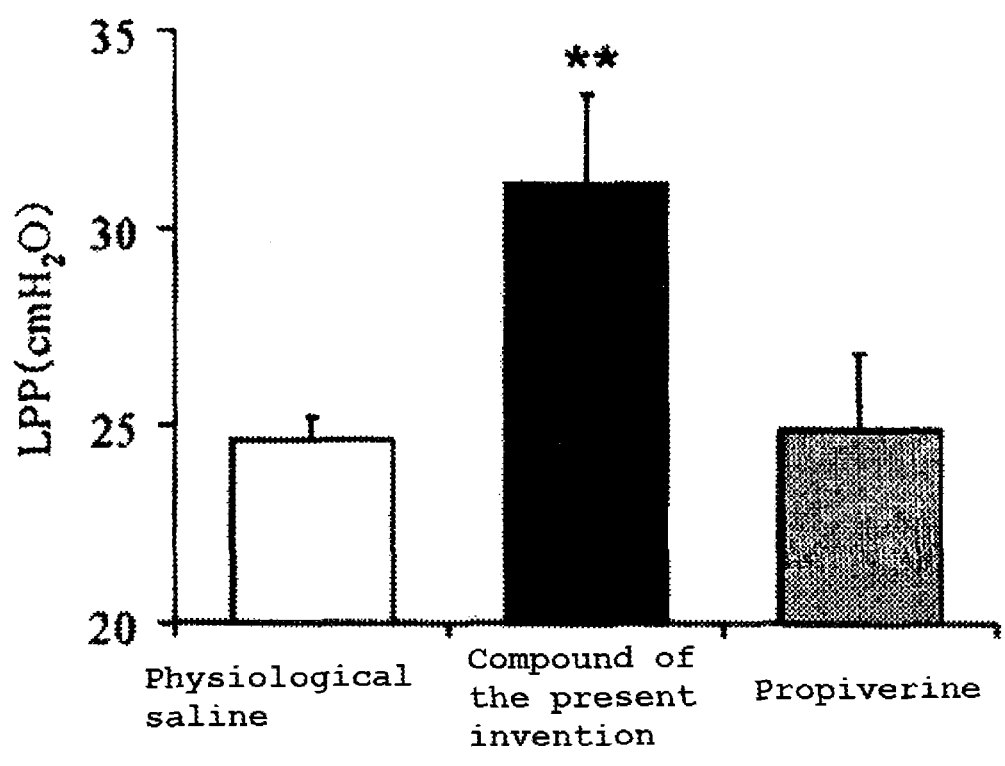
**;0.01<P, Significant difference vs saline by Dunnett's test.

PROPHYLACTIC AGENT AND/OR THERAPEUTIC AGENT FOR STRESS URINARY INCONTINENCE

CROSS REFERENCE TO RELATED APPLICATIONS

This application is a 35 U.S.C. 371 National Phase Entry Application from PCT/JP2013/063409, filed May 14, 2013, which claims the benefit of Japanese Patent Application No. 2012-111843 filed on May 15, 2012, the disclosure of which is incorporated herein in its entirety by reference.

This application claims priority to Japanese Patent Application No. 2012-111843, filed on May 15, 2012, the entire content of which is herein incorporated by reference. The present invention relates to a piperidine compound that has a superior prophylactic and/or therapeutic effect against stress urinary incontinence. The present invention particularly relates to 4-piperidyl diphenylpropoxyacetate or a salt thereof.

TECHNICAL FIELD

Background Art

Urinary incontinence is classified into urge urinary incontinence, stress urinary incontinence, overflow urinary incontinence, functional urinary incontinence, and mixed urinary incontinence. Although multiple types of urinary incontinences are involved in mixed urinary incontinence, many of the cases are a combination of urge urinary incontinence and stress urinary incontinence.

Stress urinary incontinence is leakage of urine without urge to void, due to abrupt stress on a region around the bladder/urethra in response to an action that increases abdominal pressure (e.g., coughing, sneezing, sports, or lifting something heavy). Patients with stress urinary incontinence have urethral sphincter dysfunction and/or fragile pelvic floor muscles, which results in relaxation of the urethra when abdominal pressure rises, or in incapability to contract the urethra with the same strength as the stress applied to the inside of the bladder. As a result, high abdominal pressure is applied and the rise in intravesical pressure becomes greater than the rise in the urethral pressure, thus causing leakage of urine (Non-patent Document 1).

4-piperidyl diphenylpropoxyacetate is known as a metabolite expressed in response to administration of propiverine to a rat (Non-patent Document 2). It is also reported that 4-piperidyl diphenylpropoxyacetate is produced in the human body as a metabolite, although the amount is very small (Non-patent Document 3).

Further, Patent Document 1, the object of which is to provide a compound having a superior pharmaceutical function than 1-methyl-4-piperidyl ester of O-propyl benzilic acid hydrochloride(propiverine), discloses that 4-piperidyl diphenylpropoxyacetate has a antispasmodic function on the bladder and is thus useful as a therapeutic agent for pollakiuria, nocturia, or the like caused by a cholinergic neuronal dysfunction of detrusor.

Propiverine ($\alpha,\alpha$-diphenyl-$\alpha$-n-propoxy acetic acid 1-methyl-4-piperidyl ester) is a therapeutic agent that has an anticholinergic effect and is capable of effectively treating detrusor overactivity. Thus, propiverine is effective for pollakiuria, nocturia, enuresis or the like (Patent Document 2).

A guideline for urinary incontinence in the elderly, which can be downloaded from the website of the National Center for Geriatrics and Gerontology, states that propiverine hydrochloride has direct constriction inhibition activity on the bladder detrusor, and that a therapeutic agent containing propiverine hydrochloride having an anticholinergic effect is effective for urge urinary incontinence accompanied by uninhibited contraction of the detrusor muscle. On the other hand, the guideline discloses $\alpha$-sympathetic stimulant as a therapeutic agent for stress urinary incontinence caused by urethral sphincter dysfunction, and nowhere discloses an anticholinergic agent. The guideline also states that pharmacotherapy is not appropriate for the principal therapy of stress urinary incontinence.

As described above, urge urinary incontinence and stress urinary incontinence completely differ from each other in terms of the disease mechanism. Thus, these diseases are treated with different therapeutic agents that have different action mechanisms.

Accordingly, although it is known that 4-piperidyl diphenylpropoxyacetate is effective as a therapeutic agent for pollakiuria and nocturia, which are treatable with an anticholinergic agent, its effect on stress urinary incontinence has not been suggested.

CITATION LIST

Patent Literature

Patent Document 1: JPS62-039567A
Patent Document 2: JPS55-055117A

Non-Patent Documents

Non-patent Document 1: World J Urol (1997)15, 268-274
Non-patent Document 2: J Chromatogr (1987)420, 43-52
Non-patent Document 3: European Journal of Drug Metabolism and Pharmacokinetics (1988)13(2), 81-90

SUMMARY OF THE INVENTION

Technical Problem

An object of the present invention is to provide a superior prophylactic agent and/or a therapeutic agent for stress urinary incontinence.

Solution to Problem

The inventors of the present invention carried out extensive research to attain the above object, and found that 4-piperidyl diphenylpropoxyacetate (hereinafter may also be referred to as "the compound of the present invention") represented by Formula (1) or a salt thereof has a superior therapeutic effect on stress urinary incontinence. With this finding, the inventors completed the present invention.

Specifically, the present invention provides a prophylactic agent and/or a therapeutic agent for stress urinary incontinence that comprises an effective amount of 4-piperidyl diphenylpropoxyacetate represented by Formula (1),

[Chem. 1]

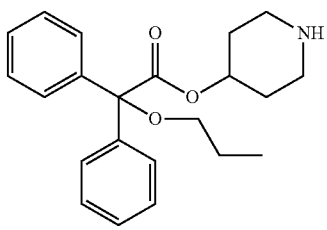

(I)

or a salt thereof, and a pharmaceutical carrier.

Further, the present invention provides a prophylactic agent and/or a therapeutic agent for stress urinary incontinence that comprises 4-piperidyl diphenylpropoxyacetate represented by Formula (1) or a salt thereof as an active ingredient.

In addition, the present invention provides a method for preventing or treating stress urinary incontinence, comprising the step of administering to a mammal 4-piperidyl diphenylpropoxyacetate represented by Formula (1) or a salt thereof, in an amount effective for the prevention or treatment of stress urinary incontinence.

Moreover, the present invention provides use of 4-piperidyl diphenylpropoxyacetate represented by Formula (1) or a salt thereof in the manufacture of a prophylactic agent or a therapeutic agent for stress urinary incontinence.

Also, the present invention provides 4-piperidyl diphenylpropoxyacetate represented by Formula (1) or a salt thereof for use in the prevention or the treatment of stress urinary incontinence.

Advantageous Effects of Invention

The compound of the present invention or a salt thereof is useful as a prophylactic agent and/or a therapeutic agent for stress urinary incontinence.

BRIEF DESCRIPTION OF DRAWINGS

FIG. 1 shows results of a test for measuring intravesical pressure when urinary leakage (leak point pressure; LPP) of a rat occurred. The results show that LPP was 24.6±0.6 cmH$_2$O for physiological saline, 31.1±2.3 cmH$_2$O for the compound of the present invention, and 24.9±1.9 cmH$_2$O for propiverine.

DESCRIPTION OF EMBODIMENTS

The 4-piperidyl diphenylpropoxyacetate or a salt thereof of the present invention is known as a metabolite that is found when propiverine is administered to rat or human. A typical production process for this is disclosed, for example, in Patent Document 1.

The compound of the present invention obtained in the above manner is capable of forming a salt, in particular, a pharmaceutically acceptable salt, through a known method.

The compound of the present invention or a salt thereof can be isolated and purified by using known separation and purification means, such as condensation, solvent extraction, filtration, recrystallization, and various kinds of chromatography.

The α,α-diphenyl-α-n-propoxy acetic acid 1-methyl-4-piperidyl ester disclosed in Patent Document 2 differs from the compound of the present invention in that a methyl group is attached to the nitrogen atom of piperidine, and its effect is "for increasing the bladder capacity after operations on the bladder and prostate, for lowering intravesical pressure due to miction (miktion) in the case of hypertonic bladder and for reducing painful bladder tenesmus of varying genesis, as well as for the treatment of pollakiuria, nocturia and nocturnal enuresis." The Examples in Patent Document 1 disclose that α,α-diphenyl-α-n-propoxy acetic acid-1-methyl-4-piperidyl ester is effective for an increase in bladder capacity and for reducing frequency of urination, and particularly effective for nocturia. It is also reported that propiverine (α,α-diphenyl-α-n-propoxy acetic acid-1-methyl-4-piperidyl ester) is useful for the treatment of stress urinary incontinence (for example, Acta Urol Jpn(1998)44, 65-69); however, as described above, the test for measuring intravesical pressure when urinary leakage (LPP) of a rat occurs clarified that the compound of the present invention has a significant alleviation effect for stress urinary incontinence, and this effect is superior to that of propiverine (Example 2).

Examples of diseases treatable by administering the therapeutic agent comprising the compound of the present invention include stress urinary incontinence. Further, since many mixed urinary incontinence cases are a combination of stress urinary incontinence and urge urinary incontinence, the therapeutic agent may also be used for the treatment of mixed urinary incontinence.

The present invention provides a pharmaceutical composition comprising an effective amount of the compound of the present invention represented by Formula (1), or a pharmaceutically acceptable salt thereof.

Examples of the pharmaceutically acceptable salt of the compound of the present invention include acid addition salts with organic acids or inorganic acids, including acid addition salts with inorganic acids such as hydrochloric acid, hydrobromic acid, hydroiodic acid, sulfuric acid, nitric acid, or phosphoric acid, and acid addition salts with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, or glutamic acid.

When the compound represented by Formula (1) or a salt thereof of the present invention is used as a medication, a pharmaceutical carrier can be added, and a suitable dosage form according to prevention and treatment purposes can be made. Examples of the dosage form include oral preparations, injections, suppositories, ointments, and patches. Of these, oral preparations are preferable. Such dosage forms can be formed by using methods conventionally known to a person skilled in the art.

As the pharmaceutical carrier, various organic or inorganic carrier materials commonly used as pharmaceutical raw materials are usable. These are used as excipients, lubricants, binders, or disintegrants in solid formulations, or as solvents, solubilizing agents, suspending agents, isotonizing agents, buffers, or soothing agents in liquid formulations, etc. If necessary, other pharmaceutical additives such as preservatives, antioxidants, colorants, sweeteners, and the like may also be used.

Oral solid formulations are prepared as follows. An excipient, optionally together with a binder, disintegrant, lubricant, colorant, sweetening/flavoring agent, etc., is added into the compound of the present invention to produce tablets, (coated or uncoated), granules, powders, capsules, or the like using a standard method. The additives used may be those commonly used in the field. Examples of usable excipients include lactose, sucrose, sodium chloride, glucose, starch, calcium carbonate, kaolin, microcrystalline cellulose, and silicic acid. Examples of usable binders include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate, and polyvinylpyrrolidone. Examples of usable disintegrants include dry starch, sodium alginate, agar powder, sodium hydrogen carbonate, calcium carbonate, sodium lauryl sulfate, stearic acid monoglyceride, and lactose. Examples of usable lubricants include purified talc, stearic acid salts, borax, and polyethylene glycol. Examples of usable colorants include titanium oxide and iron oxide. Examples of usable sweetening/flavoring agents include sucrose, wild orange peel, citric acid, and tartaric acid.

Liquid oral formulations are prepared as follows. A sweetening/flavoring agent, buffer, stabilizer, etc., are added to the compound of the present invention to produce internal liquid medicines, syrups, elixirs, or the like using a standard method. In this case, sweetening/flavoring agents as described above are usable. Examples of usable buffers include sodium citrate, etc., and examples of usable stabilizers include tragacanth, gum arabic, and gelatin.

Injections are prepared as follows. A pH adjuster, buffer, stabilizer, isotonizing agent, topical anesthetic, etc., are added to the compound of the present invention to produce subcutaneous injections, intramuscular injections, or intravenous injections using a standard method. Examples of usable pH adjusters and buffers in this case include sodium citrate, sodium acetate, and sodium phosphate. Examples of usable stabilizers include sodium pyrosulfite, EDTA, thioglycolic acid, and thiolactic acid. Examples of usable topical anesthetics include procaine hydrochloride, and lidocaine hydrochloride. Examples of usable isotonizing agents include sodium chloride and glucose.

Suppositories are prepared by first adding a pharmaceutical carrier known in related fields, such as polyethylene glycol, lanolin, cacao butter, fatty acid triglyceride, or the like, to the compound of the present invention, optionally together with Tween (®) and like surfactants, etc., and than preparing suppositories by using a standard method.

Ointments are prepared as follows. An ordinary base, stabilizer, wetting agent, preservative, etc., generally used for the compound of the present invention are added as required to the compound of the present invention, and mixed and formulated using a standard method. Examples of usable bases include liquid paraffin, white petrolatum, white beeswax, octyldodecyl alcohol, and paraffin. Examples of usable preservatives include methyl parahydroxybenzoate, ethyl parahydroxybenzoate, and propyl parahydroxybenzoate.

Patches can be prepared by coating an ordinary support with the above ointment, cream, gel, paste, etc., using a standard method. Examples of usable supports include woven or nonwoven fabrics made from cotton, staple fibers, and chemical fibers; and films and foam sheets of soft vinyl chloride, polyethylene, polyurethane, etc.

The amount of the compound of the present invention or a salt thereof to be contained in such a dosage unit form varies depending on the condition of the patient or on the dosage form. Generally, the desirable amount in one dosage unit form is about 0.01 to about 1000 mg in the case of an oral formulation, about 0.01 to about 500 mg in the case of an injection, and about 0.01 to about 1000 mg in the case of a suppository. The daily dose of the therapeutic agent in such a dosage form depends on the condition, body weight, age, gender, and the like of the patient. For example, the daily dose for an adult may be usually about 0.05 to about 5000 mg, and preferably 0.1 to 1000 mg, and is preferably administered at once or in two to four divided doses per day. In the present invention, the compound represented by Formula (1) or a salt thereof may be used solely or in a combination of two or more kinds.

Examples of mammals to which the compound of the present invention is to be administered include humans, monkeys, mice, rats, rabbits, dogs, cats, cows, horses, pigs, and sheep.

The present invention is more specifically explained below in reference to Examples and Test Examples. However, the present invention is not limited to these examples.

EXAMPLES

Example 1

Evaluation of Pharmaceutical Effect on a Stress Urinary Incontinence Model

A group consisting of eight female rats intramuscularly administered botulinum toxin A was given a subcutaneous electrical stimulus in the abdominal region so as to increase abdominal pressure, thereby expressing urinary incontinence. The compound of the present invention (30 mg/kg) was orally administered to the model rats. Further, 2 mL/kg of distilled water was orally administered to the control group, and the normal group not treated with botulinum toxin A. The frequency of urinary incontinence of each group was counted before the administration, and 30 minutes and 2 hours after the administration. Table 1 shows the results.

As shown in Table 1, although urinary incontinence was not observed in the normal group after the electrical stimulus subcutaneously delivered to the abdominal region, urinary incontinence was observed in all rats in the control group before the administration, and 30 minutes and 2 hours after the administration. In the group administered the compound of the present invention, even though urinary incontinence due to electrical stimulus was observed before the administration, the number of rats that express urinary incontinence due to the electrical stimulus was significantly decreased 2 hours after the administration of the compound of the present invention. The results showed that the compound of the present invention alleviated the symptoms of urinary incontinence of a stress urinary incontinence model.

TABLE 1

| | | Frequency of urinary incontinence | | |
| --- | --- | --- | --- | --- |
| Therapeutic agent | Number of cases | Before administration | 30 minutes after administration | 2 hours after administration |
| Normal group | 8 | 0 | 0 | 0 |
| Control group | 8 | 8 | 8 | 8 |
| Group administered the compound of the present invention | 8 | 8 | 4 | 3* |

*$p < 0.05$; Significant difference from pre-data (Fisher's exact test)

Example 2

Leak Point Pressure (LPP) of a Rat

The test for measuring intravesical pressure when urinary leakage (LPP) of a rat occurs is generally used as an in vivo test for evaluating a therapeutic effect for stress urinary incontinence (Am J Physiol Renal Physiol 293: F920-F926, 2007).

A group consisting of six or seven female SD rats was intraperitoneally administered 1.2 g/kg of urethane and anesthetized. Then, each rat was fixed prone, and the spinal cord between the ninth thoracic vertebra and the tenth thoracic vertebra was completely cut off. After hemostasis, each rat was fixed supine, and the abdominal region was cut open by median incision. The bladder was exposed and the top of the bladder was cut open, and then an indwelling catheter for measuring intravesical pressure was placed. After the operation to place the indwelling catheter, abdominal pressure was forcibly applied manually from outside. The intravesical pressure when urinary leakage occurred was monitored and used as the LPP. Physiological saline, the compound of the present invention (3 mg/kg), and propiverine (3 mg/kg) as a control therapeutic agent were intravenously administered in an amount of 1 mL/kg. Five minutes after the administration, the LPP was measured and the average value and the standard error were calculated. FIG. 1 shows the results.

The LPP was significantly higher in the group administered the compound of the present invention, compared with the physiological saline group. In contrast, there was no significant difference between the propiverine group and the physiological saline group. It was thus revealed that the compound of the present invention has an excellent therapeutic effect for stress urinary incontinence, and this effect is superior to that of propiverine.

INDUSTRIAL APPLICABILITY

The compound represented by Formula (1) or a salt thereof of the present invention is useful as a prophylactic agent and/or a therapeutic agent for stress urinary incontinence.

What is claimed is:

1. A method for treating stress urinary incontinence, comprising the step of administering to a mammal 4-piperidyl diphenyipropoxyacetate represented by Formula (1),

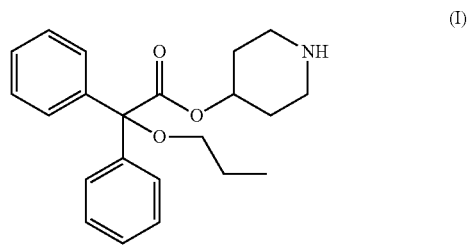 [SMILES: CCCOC(C(=O)OC1CCNCC1)(c1ccccc1)c1ccccc1]

or a salt thereof, in an amount effective for the treatment of stress urinary incontinence, in combination with a pharmaceutical carrier.

* * * * *